US008784877B2

(12) United States Patent
Houze et al.

(10) Patent No.: US 8,784,877 B2
(45) Date of Patent: Jul. 22, 2014

(54) TRANSDERMAL LEVONORGESTREL DEVICE AND DELIVERY

(75) Inventors: David W. Houze, Miami, FL (US); Vincent Lau Chan, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 71 days.

(21) Appl. No.: 13/337,594

(22) Filed: Dec. 27, 2011

(65) Prior Publication Data

US 2012/0189686 A1 Jul. 26, 2012

Related U.S. Application Data

(63) Continuation of application No. PCT/US2011/067109, filed on Dec. 23, 2011.

(60) Provisional application No. 61/428,061, filed on Dec. 29, 2010.

(51) Int. Cl.
*A61K 9/70* (2006.01)

(52) U.S. Cl.
USPC .......................................... 424/448; 514/179

(58) Field of Classification Search
None
See application file for complete search history.

(56) References Cited

U.S. PATENT DOCUMENTS

| | | | |
|---|---|---|---|
| 5,595,759 A * | 1/1997 | Wright et al. ................. | 424/464 |
| 5,656,286 A | 8/1997 | Miranda et al. | |
| 6,024,976 A | 2/2000 | Miranda | |
| 6,221,383 B1 | 4/2001 | Miranda et al. | |
| 7,456,159 B2 | 11/2008 | Houze et al. | |
| 7,846,916 B2 | 12/2010 | Houze | |
| 7,867,986 B2 | 1/2011 | Houze | |
| 7,879,831 B2 | 2/2011 | Houze | |
| 8,025,898 B2 | 9/2011 | Houze et al. | |
| 8,110,565 B2 | 2/2012 | Houze et al. | |
| 2001/0009673 A1 * | 7/2001 | Lipp et al. ..................... | 424/400 |
| 2002/0058058 A1 * | 5/2002 | Mantelle et al. .............. | 424/449 |
| 2004/0142914 A1 * | 7/2004 | Friedman et al. ............. | 514/170 |
| 2006/0240087 A1 * | 10/2006 | Houze et al. .................. | 424/449 |
| 2008/0262445 A1 * | 10/2008 | Hsu et al. ..................... | 604/307 |

OTHER PUBLICATIONS

Anderson, F., "Selectivity and minimal androgenicity of norgestimate in monophasic and triphasic oral contraceptives," Acta Obstet Gynecol Scand Suppl 156: 15-21 (1992) (Abstract).*
Norgestimate, available at http://en.wikipedia.org/wiki/Norgestimate, accessed Nov. 3, 2012.*
Bialy et al., "Structure Activity Relationships in a Series of Norethisterone and Levonorgestrel Esters," Steroids, vol. 41, No. 3, pp. 419-439, Mar. 1, 1983.
Karunanithy et al., "Correlation of contraceptive activity of norethisterone and levonorgestrel esters with VR(W) values and hydrolysis rates," Journal of Pharmacobio-Dynamics, vol. 12, No. 8, pp. 468-475, Jan. 1, 1989.
International Search Report issued on May 14, 2012 in application No. PCT/US2011/067109.

* cited by examiner

*Primary Examiner* — David J Blanchard
*Assistant Examiner* — Daniel F Coughlin
(74) *Attorney, Agent, or Firm* — Foley & Lardner LLP

(57) ABSTRACT

Described are transdermal drug delivery systems for the transdermal administration of levonorgestrel, comprising a polymer matrix and levonorgestrel acetate. Methods of making and using such systems also are described.

14 Claims, 2 Drawing Sheets

TRANSDERMAL LEVONORGESTREL DEVICE AND DELIVERY

RELATED APPLICATION

This application is a continuation of International Application serial number PCT/US11/67109, filed Dec. 23, 2011, and claims priority to U.S. Provisional Application Ser. No. 61/428,061, filed Dec. 29, 2010, the entire contents of which are incorporated herein by reference in their entirety.

FIELD OF THE INVENTION

Described herein are compositions and methods for the transdermal delivery of levonorgestrel.

BACKGROUND

This invention relates generally to transdermal drug delivery systems, and more particularly, to transdermal drug delivery systems for the delivery of levonorgestrel. The use of a transdermal system, for example, a patch comprising a pressure-sensitive adhesive containing a drug, as a means of delivering drug through the skin is well known. However, there remains a need for transdermal drug delivery systems designed for the delivery of specific drugs, such as levonorgestrel, and there remains a particular need for smaller transdermal drug delivery systems that exhibit desired pharmacokinetic properties.

Transdermal delivery systems (adhesive patches) as dosage forms have been the subject of a vast number of patent applications over the last 25 years, yielding many patents but few commercial products in comparison. To those working in the field, the relatively small number of commercial products is not surprising. Although regulatory, economic, and market hurdles play a role in limiting the number of products on the market, the task of developing a transdermal delivery system that achieves desired physical and pharmacokinetic parameters to satisfy physician and patient demand is more daunting. Parameters to be considered during commercial product development may include drug solubility, drug stability (e.g., as may arise from interaction with other component materials and/or the environment), delivery of a therapeutic amount of drug at a desired delivery rate over the intended duration of use, adequate adhesion at the anatomical site of application, integrity (e.g., minimal curling, wrinkling, delaminating and slippage) with minimal discomfort, irritation and sensitization both during use and during and after removal, and minimal residual adhesive (or other components) after removal. Size also may be important from a manufacturing and patient viewpoint, and appearance may be important from a patient viewpoint. The physical manufacturing and production aspects of commercial product development (e.g., the identity and costs of materials, equipment, and labor) and supporting analytical methods required for regulatory compliance also can be significant.

Of the physical parameters that are considered when developing a commercial transdermal drug delivery system, size, e.g., surface area at the site of application, is often dictated and limited by other physical and pharmacokinetic requirements, such as desired drug delivery rates and daily dosages. In general, it is easier to develop a relatively "large" transdermal drug delivery system that will achieve drug delivery at target therapeutic levels over an intended duration of therapy, than it is to develop a smaller transdermal drug delivery system that still exhibits acceptable pharmacokinetic properties. Still, because size directly impacts costs (e.g., costs of component materials, costs of packaging materials, costs for production and manufacturing equipment, labor costs relative to product yield per run time, etc.) and patients generally prefer smaller systems to larger ones (both for aesthetic reasons and comfort, since a smaller surface may permit the use of less aggressive adhesives), there is a need for smaller transdermal drug delivery systems.

SUMMARY

In accordance with one embodiment, there is provided a transdermal drug delivery system comprising a polymer matrix comprising levonorgestrel acetate in an amount at or below its saturation concentration in the polymer matrix. In some embodiments, the transdermal drug delivery system comprises from about 1% to about 15% by weight levonorgestrel acetate, based on the total dry weight of the polymer matrix, including from about 1% to about 8% by weight, about 1% to about 6% by weight, about 1% to about 3% by weight, or about 2% to about 6% by weight.

In accordance with some embodiments, the polymer matrix comprises a pressure-sensitive adhesive polymer, such as one that comprises a polymer selected from the group consisting of a silicone polymer, an acrylic polymer, a soluble polyvinylpyrimidine (PVP), and mixtures of one or more thereof. In some embodiments, the polymer matrix comprises about 5-60% by weight acrylic adhesive, about 20-80% by weight silicone adhesive, about 1-20% by weight soluble PVP, up to about 15% by weight penetration enhancer, and about 1-15% by weight levonorgestrel acetate, all based on the total dry weight of the polymer matrix. In specific embodiments, the polymer matrix comprises about 5% by weight acrylic adhesive, about 74% by weight silicone adhesive, about 10% by weight soluble PVP, about 8.0% by weight oleyl alcohol, and about 3% by weight levonorgestrel acetate.

In accordance with some embodiments, the transdermal drug delivery system exhibits a greater flux of the levonorgestrel acetate active agent than a corresponding transdermal drug delivery system comprising levonorgestrel as the active agent, wherein the transdermal drug delivery systems each comprise amounts of levonorgestrel acetate or levonorgestrel, respectively, that are at or near but below the active agent's saturation concentration in the polymer matrix.

In accordance with some embodiments, the transdermal drug delivery system delivers at least the same amount of the levonorgestrel acetate active agent as a corresponding transdermal drug delivery system comprising levonorgestrel as the active agent and having an active surface area at least about 1.33 times larger than the active surface area of the levonorgestrel acetate transdermal drug delivery system, where the active surface area is defined by the surface area of the polymer matrix, and wherein the transdermal drug delivery systems each comprise amounts of levonorgestrel acetate or levonorgestrel, respectively, that are at or near but below the active agent's saturation concentration in the polymer matrix.

In accordance with other embodiments, there is provided a method of preventing or treating a condition subject to prevention or treatment by levonorgestrel, comprising administering a levonorgestrel acetate transdermal drug delivery system as described herein. In some embodiments, the method provides contraception or hormone replacement therapy.

In accordance with other embodiments, there is provided a method of enhancing transdermal drug delivery of levonorgestrel, comprising providing a levonorgestrel acetate transdermal drug delivery system as described herein.

DETAILED DESCRIPTION

Figure 1:
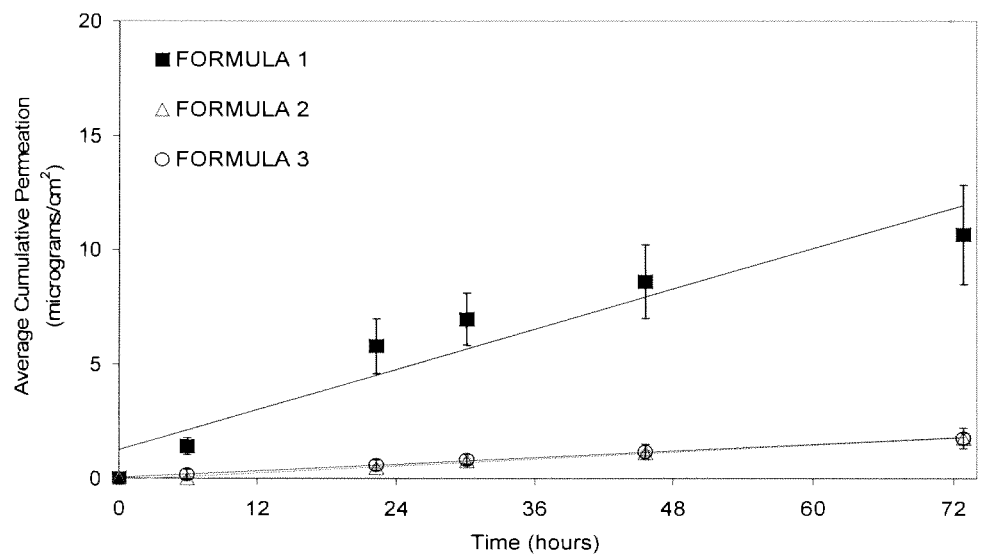
FIG. 1 illustrates the cumulative permeation flux ($\mu g/cm^2$) of levonorgestrel over time (0-72 hours) from a transdermal delivery systems comprising a drug-in-adhesive polymer matrix with 0.5% (■), 0.75% (△) and 1.0% (○) by weight levonorgestrel, based on the weight of the polymer matrix.

The field of transdermal delivery systems suffers from the problem of needing to balance many different competing factors to develop a commercial product that exhibits, for example both clinical efficacy and satisfactory wear properties while remaining acceptable to patients. For example, when selecting the size of a transdermal delivery system, it is necessary to balance factors that favor a smaller size (such as lower cost, better adhesive performance and improved aesthetics) against factors that favor a larger size (such as the target delivery rate (flux) and daily dose).

While many of the common hormonal contraceptives are a combination of progesterone and estrogen, there are several benefits to utilizing a progesterone-only contraceptive (POC). POCs are not associated with an increased risk of blood clots or raising blood pressure. They are also not associated with an increased incidence of stroke.

Levonorgestrel is a synthetic progestin used in various hormonal contraceptives, including emergency contraceptives, and hormone replacement therapy (HRT). When adherence to the usage schedule is strictly followed, a progestin-only hormonal contraceptive proves to be equally as effective as the combination oral pill and combination transdermal patch. A transdermal delivery system comprising levonorgestrel and estradiol is sold under the name Climara Pro® (Bayer HealthCare Pharmaceuticals, Inc.).

The present inventors surprisingly discovered that levonorgestrel acetate, a pro-drug of levonorgestrel, exhibits improved flux from a transdermal delivery system as compared to levonorgestrel, to an extent that permits the use of a smaller transdermal delivery system (based on active surface area). Thus, for example, in accordance with the invention described herein, a transdermal delivery system comprising levonorgestrel acetate can have a smaller active surface area than a corresponding system comprising levonorgestrel but achieve the delivery of daily dosages that are about equal to or greater than the levonorgestrel product. For example, the present invention includes transdermal drug delivery systems that achieve the delivery of daily dosages that are about equal to a corresponding levonorgestrel product, in a smaller sized system, such as where the levonorgestrel system is about 1.33 times the size of the levonorgestrel acetate system (or the levonorgestrel acetate system is about 77% the size of the levonorgestrel system), based on active surface area. In other words, the present invention permits a patch size reduction of about one third (including about 37%), without sacrificing therapeutic efficacy. The ability to provide a smaller system without sacrificing daily dosage represents a significant advance over the state of the art. Additionally or alternatively, in accordance with the invention described herein, a transdermal delivery system comprising levonorgestrel acetate can achieve drug delivery over an extended period of time, including achieving the delivery of a therapeutically effective amount of levonorgestrel acetate over an extended period of 24 hours or longer, including 3 days or longer. The ability to provide a product for extended use also represents a significant advance over the state of the art.

DEFINITIONS

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described composition (e.g., transdermal drug delivery system, polymer matrix, etc.) comprises less than about 5%, less than about 3%, or less than about 1% by weight, based on the total weight of the composition at issue, of the excluded component.

As used herein "subject" denotes any animal in need of drug therapy, including humans. For example, a subject may be suffering from or at risk of developing a condition that can be treated or prevented with levonorgestrel, or may be taking levonorgestrel for health maintenance purposes.

As used herein, the phrases "therapeutically effective amount" and "therapeutic level" mean that drug dosage or plasma concentration in a subject, respectively, that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing layer of the transdermal drug delivery system.

As used herein, "levonorgestrel" includes 13-ethyl-17-ethynyl-17-hydroxy-1,2,6,7,8,9,10,11,12,13,14,15,16,17-tetradecahydrocyclopenta[α]phenanthren-3-one:

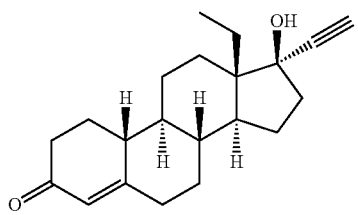

As used herein, "flux" (also called "permeation rate") is defined as the absorption of a drug through skin or mucosal tissue, and is described by Fick's first law of diffusion:

$$J = -D(dCm/dx)$$

where J is the flux in $g/cm^2/sec$, D is the diffusion coefficient of the drug through the skin or mucosa in $cm^2/sec$ and $dCm/dx$ is the concentration gradient of the drug across the skin or mucosa.

As used herein, the term "transdermal" refers to delivery, administration or application of a drug by means of direct contact with skin or mucosa. Such delivery, administration or application is also known as dermal, percutaneous, transmucosal and buccal. As used herein, "dermal" includes skin and mucosa, which includes oral, buccal, nasal, rectal and vaginal mucosa.

As used herein, "transdermal drug delivery system" refers to a system (e.g., a device) comprising a composition that releases an active agent (such as levonorgestrel or levonorgestrel acetate) upon application to the skin (or any other surface noted above). A transdermal drug delivery system may comprise a backing layer, a drug-containing layer, and a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. As described below, in one embodiment, the transdermal drug delivery system comprises a drug-containing polymer matrix that comprises a pressure-sensitive adhesive or bioadhesive, and is adopted for direct application to a user's (e.g., a subject's) skin. In other embodiments, the polymer matrix is non-adhesive and may be provided with separate adhesion means (such as a separate adhesive layer) for application and adherence to the user's skin.

As used herein, "polymer matrix" refers to a polymer composition which contains one or more drugs. In some embodiments, the matrix comprises a pressure-sensitive adhesive polymer or a bioadhesive polymer. In other embodiments, the matrix does not comprise a pressure-sensitive adhesive or bioadhesive. As used herein, a polymer is an "adhesive" if it has the properties of an adhesive per se, or if it functions as an adhesive by the addition of tackifiers, plasticizers, crosslinking agents or other additives. Thus, in some embodiments, the polymer matrix comprises a pressure-sensitive adhesive polymer or a bioadhesive polymer, with levonorgestrel dissolved or dispersed therein. The polymer matrix also may comprise tackifiers, plasticizers, crosslinking agents or other additives described herein. U.S. Pat. No. 6,024,976 describes polymer blends that are useful in accordance with the transdermal systems described herein. The entire contents of U.S. Pat. No. 6,024,976 is incorporated herein by reference.

As used herein, the term "pressure-sensitive adhesive" refers to a viscoelastic material which adheres instantaneously to most substrates with the application of very slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

The term pressure-sensitive adhesive also includes mixtures of different polymers and mixtures of polymers, such as polyisobutylenes (PIB), of different molecular weights, wherein each resultant mixture is a pressure-sensitive adhesive. In the last case, the polymers of lower molecular weight in the mixture are not considered to be "tackifiers," said term being reserved for additives which differ other than in molecular weight from the polymers to which they are added.

In some embodiments, the polymer matrix is a pressure-sensitive adhesive at room temperature and has other desirable characteristics for adhesives used in the transdermal drug delivery art. Such characteristics include good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and 0° C.

As used herein, the term "rubber-based pressure-sensitive adhesive" refers to a viscoelastic material which has the properties of a pressure-sensitive adhesive and which contains at least one natural or synthetic elastomeric polymer.

In some embodiments, the transdermal drug delivery system includes one or more additional layers, such as one or more additional polymer matrix layers, or one or more adhesive layers that adhere the transdermal drug delivery system to the user's skin. In other embodiments, the transdermal drug delivery system is monolithic, meaning that it comprises a single polymer matrix layer comprising a pressure-sensitive adhesive or bioadhesive with drug dissolved or dispersed therein, and no rate-controlling membrane.

The transdermal drug delivery system also may include a drug impermeable backing layer or film. In some embodiments, the backing layer is adjacent one face of the polymer matrix layer. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, nonwoven fabric, cloth and commercially available laminates. A typical backing material has a thickness in the range of 2 to 1000 micrometers.

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-Off® 7610 and 3M's 1022 Scotch Pak.

A used herein, a "monolithic" transdermal drug delivery system may include a backing layer and/or release liner.

In accordance with some embodiments, the transdermal dug delivery system comprises a drug-containing polymer matrix layer that comprises a pressure-sensitive adhesive blend comprising an acrylic polymer, a silicone polymer, and a soluble PVP.

Acrylic Polymers

The term "acrylic polymer" is used here as in the art interchangeably with "polyacrylate," "polyacrylic polymer," and "acrylic adhesive." The acrylic-based polymers can be any of the homopolymers, copolymers, terpolymers, and the like of various acrylic acids or esters. In some embodiments, the acrylic-based polymers are adhesive polymers. In other embodiments, the acrylic-based polymers function as an adhesive by the addition of tackifiers, plasticizers, crosslinking agents or other additives.

The acrylic polymer can include copolymers, terpolymers and multipolymers. For example, the acrylic polymer can be any of the homopolymers, copolymers, terpolymers, and the like of various acrylic acids. In some embodiments, the acrylic polymer constitutes up to about 60% by weight of the polymer matrix, including about 5% to about 60%, based on the dry weight of the polymer matrix. In some embodiments, the amount and type of acrylic polymer is dependent on the amount of levonorgestrel acetate used and/or the amount of polysiloxane polymer used.

Acrylic polymers useful in practicing the invention include polymers of one or more monomers of acrylic acids and other copolymerizable monomers. The acrylic polymers also include copolymers of alkyl acrylates and/or methacrylates and/or copolymerizable secondary monomers or monomers with functional groups. Combinations of acrylic-based polymers based on their functional groups is also contemplated. Acrylic-based polymers having functional groups include copolymers and terpolymers which contain, in addition to nonfunctional monomer units, further monomer units having free functional groups. The monomers can be monofunctional or polyfunctional. By varying the amount of each type of monomer added, the cohesive properties of the resulting acrylic polymer can be changed as is known in the art. In some embodiments, the acrylic polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid and methacrylic acid and alkyl acrylic or methacrylic esters such as methyl acrylate, ethyl acrylate, propyl acrylate, amyl acrylate, butyl acrylate, butyl methacrylate, hexyl acrylate, hexyl methacrylate, heptyl acrylate, octyl acrylate, nonyl acrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, glycidyl acrylate, and corresponding methacrylic esters.

Non-functional acrylic-based polymers can include any acrylic based polymer having no or substantially no free functional groups.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

As used herein, "functional monomers or groups," are monomer units typically in acrylic-based polymers which have reactive chemical groups which modify the acrylic-based polymers directly or which provide sites for further reactions. Examples of functional groups include carboxyl, epoxy, hydroxyl, sulfoxyl, and amino groups. Acrylic-based polymers having functional groups contain, in addition to the nonfunctional monomer units described above, further monomer units having free functional groups. The monomers can be monofunctional or polyfunctional. These functional groups include carboxyl groups, hydroxy groups, amino groups, amido groups, epoxy groups, etc. Typical carboxyl functional monomers include acrylic acid, methacrylic acid, itaconic acid, maleic acid, and crotonic acid. Typical hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. As noted above, in some embodiments, the acrylic polymer does not include such functional groups.

Further details and examples of acrylic adhesives which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989); "Acrylic and Methacrylic Ester Polymers," *Polymer Science and Engineering*, Vol. 1, 2nd ed., pp 234-268, John Wiley & Sons, (1984); U.S. Pat. No. 4,390,520; and U.S. Pat. No. 4,994,267, all of which are expressly incorporated by reference in their entireties.

Suitable acrylic polymers also include pressure-sensitive adhesives which are commercially available, such as the acrylic-based adhesives sold under the trademarks Duro-Tak® by National Starch and Chemical Corporation, Bridgewater, N.J. (such as Duro-Tak® 87-2287, -4098, -2852, -2196, -2296, -2194, -2516, -2070, -2353, -2154, -2510, -9085, -9088 and 73-9301). Other suitable acrylic adhesives include those sold under the trademark Eudragit® by Roehm Pharma GmbH, Darmstadt, Germany, those sold by Cytec Surface Specialties, St. Louis, Mo., under the trademarks Gelva® Multipolymer Solution (such as Gelva® 2480, 788, 737, 263, 1430, 1753, 1151, 2450, 2495, 3067, 3071, 3087 and 3235). For example, hydroxy functional adhesives with a reactive functional OH group in the polymeric chain, can be used. Non-limiting commercial examples of this type of adhesives include both Gelva® 737, 788, and 1151, and Duro-Tak® 87-2287, -4287, -2510 and -2516.

Silicon Polymers

The term "silicone-based" polymer is used interchangeably with the terms siloxane, polysiloxane, and silicones as used herein and as known in the art. A suitable silicone-based polymer may also be a pressure-sensitive adhesive. Thus, in some embodiments, the silicone-based polymer is an adhesive polymer. In other embodiments, the silicone-based polymer functions as an adhesive by the addition of tackifiers, plasticizers, crosslinking agents, or other additives.

Suitable polysiloxanes include silicone pressure-sensitive adhesives which are based on two major components: (i) a polymer or gum and (ii) a tackifying resin. A polysiloxane adhesive can be prepared by cross-linking a gum, typically a high molecular weight polydiorganosiloxane, with a resin, to produce a three-dimensional silicate structure, via a condensation reaction in an appropriate organic, volatile solvent, such as ethyl acetate or heptane. The ratio of resin to polymer can be adjusted in order to modify the physical properties of polysiloxane adhesives. Sobieski, et al., "Silicone Pressure Sensitive Adhesives," Handbook of Pressure-Sensitive Adhesive Technology, 2nd ed., pp. 508-517 (D. Satas, ed.), Van Nostrand Reinhold, New York (1989).

Exemplary silicone-based polymers are adhesives (e.g., capable of sticking to the site of topical application), including pressure-sensitive adhesives. Illustrative examples of silicone-based polymers having reduced silanol concentrations include silicone-based adhesives (and capped polysiloxane adhesives) such as those described in U.S. Pat. No. Re. 35,474 and U.S. Pat. No. 6,337,086, which are incorporated herein by reference in their entireties, and which are commercially available from Dow Corning Corporation (Dow Corning Corporation, Medical Products, Midland, Mich.) as Bio-PSA® 7-4100, -4200 and -4300 product series, and non-sensitizing, pressure-sensitive adhesives produced with compatible organic volatile solvents (such as ethyl acetate or heptane) and available commercially under their Bio-PSA® 7-4400 series, -4500 series and -4600 series.

Further details and examples of silicone pressure-sensitive adhesives which are useful in the polymer matrices and compositions and methods described herein are mentioned in the following U.S. Pat. Nos. 4,591,622; 4,584,355; 4,585,836; and 4,655,767, which are all expressly incorporated by reference herein in their entireties. It should also be understood that silicone fluids are also contemplated for use in the polymer matrices and methods described herein.

In some embodiments, the polysiloxane constitutes up to about 80% by weight of the polymer matrix, including about 20% to about 80% and about 20% to about 75%, based on the dry weight of the polymer matrix. In some embodiments, the amount and type of polysiloxane is dependent on the amount and type of acrylic polymer and/or the amount of levonorgestrel acetate used. For example, in some embodiments, the amount of acrylic-based polymer and silicone-based polymer can be adjusted so as to modify the saturation concentration of the drug in the polymer matrix in order to affect the rate of delivery of the drug from the system and through the skin.

Soluble PVP

In some embodiments, the polymer matrix includes soluble PVP. Soluble PVP has been found to be highly effective in preventing crystallization of drugs, such as levonorgestrel, in adhesive-type transdermal drug delivery system. Soluble PVP also may modulate the transdermal permeation rate of the drug.

The term "PVP or "polyvinylpyrrolidone" refers to a polymer, either a homopolymer or copolymer, containing N-vinylpyrrolidone as the monomeric unit. Typical PVP polymers are homopolymeric PVPs and the copolymer vinyl acetate vinylpyrrolidone. The homopolymeric PVPs are known to the pharmaceutical industry under a variety of designations including Povidone, Polyvidone, Polyvidonum, Polyvidonum soluble, and Poly(1-vinyl-2-pyrrolidone). The copolymer vinyl acetate vinylpyrrolidone is known to the pharmaceutical industry as Copolyvidon, Copolyvidone, and Copolyvidonum. The term "soluble" when used with reference to PVP means that the polymer is soluble in water and generally is not substantially cross-linked, and has a molecular weight of less than about 2,000,000. See, generally, Buhler, Kollidon®: POLYVINYLPRYRROLIDONE FOR THE PHARMACEUTICAL INDUSTRY, BASF Aktiengesellschaft (1992).

The amount and type of soluble PVP used may depend on the quantity of levonorgestrel acetate present, as well as the type of adhesive, but can be readily determined through routine experimentation. Typically, the PVP is present in an amount of up to about 20%, such as from about 1% to about 20%, from about 5% to about 15% by weight, or about 10% by weight, based on the total dry weight of the polymer matrix. However, the amount of PVP can be higher than 20% for example, up to 40%, depending on the desired properties of the blend. The soluble PVP may have a molecular weight of about 2,000 to 1,100,000, including 5,000 to 100,000, and 7,000 to 54,000. In some embodiments, the soluble PVP has a molecular weight of from about 17,000 to about 90,000, such as from about 17,000 to about 60,000, including from 17,000 to 90,000 and from 17,000 to 60,000.

In some embodiments, the polymer matrix comprises a soluble PVP with a rubber-based pressure-sensitive adhesive and a polyacrylate polymer, such as a blend of an acrylic polymer, a polysiloxane and a soluble PVP, as each are described individually above. In some embodiments, the blend is chosen to affect the rate of drug delivery. More specifically, a plurality of polymers including a soluble polyvinylpyrrolidone, which may have different solubility parameters for the drug and which may be immiscible with each other, may be selected to adjust the solubility of the drug in the polymer matrix, thereby controlling the maximum concentration of the drug in the system, and modulating drug delivery through the dermis.

Levonorgestrel Acetate

The polymer matrix includes levonorgestrel acetate in a therapeutically effective amount.

The present inventors surprisingly discovered that there is a saturation point where further drug loading of levonorgestrel acetate (or levonorgestrel) leads to a significant drop in flux rate. This effect is not observed with all transdermal drug delivery systems. For example, with some drugs it can be advantageous to provide an amount of drug in excess of the saturation concentration, and such excess drug loading can result in enhanced flux properties.

Thus, in accordance with some embodiments, the drug loading (amount of levonorgestrel acetate) is selected so as to include an amount of levonorgestrel acetate that is at, near but below, or below the saturation concentration of levonorgestrel acetate in the polymer matrix, such as being at or near but below the saturation concentration.

In some embodiments, the concentration by weight of the levonorgestrel acetate in the transdermal drug delivery is about 1% to about 15%, including from about 1% to about 8% by weight, about 1% to about 6% by weight, about 1% to about 3% by weight, or about 2% to about 6% by weight, about 1.0%, about 1.5%, about 2.0%, about 2.5%, about 3.0%, about 3.5%, about 4.0%, about 4.5%, or about 5.0%, all based on the total dry weight of the polymer matrix. Irrespective of whether there is high-loading or low-loading of the levonorgestrel acetate into the transdermal drug delivery system, the pressure-sensitive adhesive composition can be formulated to maintain acceptable shear, tack, and peel adhesive properties.

The amount of levonorgestrel acetate to be incorporated in the polymer matrix also may be adjusted depending on the desired therapeutic effect, and the time span for which the system is to provide therapy. For most drugs, the passage of the drugs through the skin will be the rate-limiting step in delivery. A minimum amount of drug in the system is selected based on the amount of drug which passes through the skin in the time span for which the system is to provide therapy. In some embodiments, a system for the transdermal delivery of levonorgestrel acetate is used over a period of about 1 day, about 3 days, about 7 days, or longer. Thus, in one embodiment, the systems comprise an amount of drug (e.g., levonorgestrel acetate) sufficient to deliver therapeutically effective amounts of drug over a period of from 1 day to 3 days, 7 days, or longer, including for 1 day, for 2 days, for 3 days, for 4 days, for 5 days, for 6 days, for 7 days, or for longer.

In some embodiments, the transdermal levonorgestrel acetate delivery system is smaller (based on active surface area) than a levonorgestrel product that achieves comparable drug delivery. For example, in some embodiments a transdermal drug delivery system according to the invention may contain an amount of levonorgestrel acetate effective to deliver an amount of active agent comparable to that delivered from a corresponding levonorgestrel system that is 1.33 times larger than the levonorgestrel acetate system, or the levonorgestrel acetate system may achieve a comparable drug delivery (e.g. of a comparable therapeutic dose) while being 77% the size of the levonorgestrel system. In this context, a "corresponding" system can be a system with a polymer matrix that is comprised of the same polymer components in approximately the same amounts with an amount of drug (levonorgestrel acetate or levonorgestrel) that is at or near but below the saturation concentration of the drug in the polymer matrix. The preparation of corresponding levonorgestrel and levonorgestrel acetate compositions is illustrated in the examples.

Other Components

In one embodiment, the polymer matrix comprises a penetration enhancer. A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skin including the boundary layer.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In one embodiment, the penetration enhancer is oleyl alcohol. In another embodiment, the penetration enhancer is a glycol, such as dipropylene glycol, propylene glycol, butylene glycol or polyethylene glycol. In other embodiments, the penetration enhancer comprises a mixture of at least two penetration enhancers. For example, a penetration enhancer may comprise oleyl alcohol and one or more polyhydric alcohols, such as glycerine, dipropylene glycol, butylene glycol, propylene glycol. For instance, the penetration enhancer may include oleyl alcohol and dipropylene glycol.

In some embodiments, a penetration enhancer is used in an amount up to about 15% by dry weight of the polymer matrix, including up to about 10% by weight, based on the dry weight of the polymer matrix. In some embodiments, a penetration enhancer is used in an amount of from about 5% to about 15%, such as from 5% to 15%, or about 10%. In specific embodiments, the penetration enhancer comprises oleyl alcohol and amounts to about 8% by weight of the polymer matrix. The polymer matrix may further comprise various thickeners, fillers, and other additives or components known for use in transdermal drug delivery systems.

In some embodiments, the polymer matrix comprises about 5-60% by weight acrylic adhesive, about 20-80% by weight silicone adhesive, about 1-20% by weight soluble PVP, up to about 15% by weight penetration enhancer, and about 1-15% by weight levonorgestrel acetate, all based on the total dry weight of the polymer matrix. In specific embodiments, the polymer matrix comprises about 5% by weight acrylic adhesive, about 74% by weight silicone adhesive, about 10% by weight soluble PVP, about 8.0% by weight oleyl alcohol, and about 3% by weight levonorgestrel acetate.

As noted above, in embodiments where the polymer matrix comprises a pressure-sensitive adhesive or bioadhesive, the polymer matrix can serve as an adhesive portion of the system (e.g., a reservoir device), or can serve as one or more layers of a multi-layer system. Alternatively, a polymer matrix comprising a pressure-sensitive adhesive or bioadhesive with drug dissolved or dispersed therein can constitute a monolithic device. In embodiments where the polymer matrix does not comprise an adhesive, but instead, for example, comprises a polymeric drug reservoir, it can be used in combination with one or more adhesive layers, or with a surrounding adhesive portion, as is well known to those skilled in the art.

In some embodiments, the system consists essentially of the polymer matrix layer. By "consists essentially of the polymer matrix layer" means that the system does not contain any other layers that affect drug delivery, such as an additional rate-controlling polymer layer, rate-controlling membrane, or drug reservoir layer. It will be understood, however, that the system that consists essentially of the polymer matrix layer may comprise a backing layer and/or release liner.

As discussed above, in some embodiments, the levonorgestrel acetate transdermal systems described herein have a greater flux than corresponding levonorgestrel systems (when both products are formulated in corresponding polymer matrices with an amount of drug that is at or near but below the saturation point of the drug in the polymer matrix) and, therefore, exhibit increased drug delivery per unit area of the active surface area. For example, in some embodiments, a levonorgestrel acetate transdermal system achieves a drug delivery that is comparable to (e.g., about the same flux and/or about the same cumulative amount of drug delivered) a levonorgestrel product that is 1.33 times larger (based on the active surface area). In other words, in some embodiments the levonorgestrel acetate transdermal systems described herein can be 77% the size of (or about one third of or about 37% smaller than) a levonorgestrel product but achieve the same therapeutic effect.

Additionally or alternatively, in accordance with some embodiments, the levonorgestrel acetate transdermal systems described herein can achieve drug delivery over an extended period of time, including achieving the delivery of a therapeutically effective amount of levonorgestrel acetate over an extended period of 24 hours or longer, 24 hours, 36 hours, 48 hours, 60 hours, 72 hours (3 days), or longer.

The system may be of any shape or size suitable for transdermal application. In some embodiments, the systems are smaller than a levonorgestrel product, but achieve comparable daily dosages. For example, the systems may have an active surface area of 0.9, 0.8, 0.7, 0.75, 0.66, 0.6, 0.5, 0.4, 0.33, 0.3, 0.25, 0.2, or 0.1 times the active surface area of a levonorgestrel product. In some embodiments, the system has an active surface area that is about 80% or about 77% the size of a levonorgestrel product, such as about 80%, 77%, about 75%, about 67%, about 66%, about 65% or about 60% of a product that delivers a comparable amount (e.g., a comparable therapeutic dosage) of levonorgestrel.

The polymer matrices described herein may be prepared by methods known in the art. The polymer matrices can be formed into systems by methods known in the art. For example, the polymer matrix material can be applied to a backing layer and release liner by methods known in the art, and formed into sizes and shapes suitable for use.

For example, after the polymer matrix is formed, it may be brought into contact with a support layer, such a releaser liner layer or backing layer, in any manner known to those of skill in the art. Such techniques include calender coating, hot melt coating, solution coating, etc.

For example, a polymer matrix can be prepared by blending the components of the polymer matrix, applying the matrix material to a support layer such as a backing layer or release liner, and removing any remaining solvents. The levonorgestrel acetate can be added at any stage. In one embodiment, all polymer matrix components, including levonorgestrel acetate, are blended together. In another embodiment, the polymer matrix components other than levonorgestrel acetate are blended together, and then the levonorgestrel acetate is dissolved or dispersed therein. The order of steps, amount of ingredients, and the amount and time of agitation or mixing can be determined and optimized by the skilled practitioner. An exemplary general method is as follows:

Appropriate amounts of soluble PVP, solvent(s), enhancer(s), and organic solvent(s) (for example toluene) are combined and thoroughly mixed together in a vessel.

Levonorgestrel acetate is then added to the mixture and agitation is carried out until the drug is uniformly mixed in.

Appropriate amounts of polysiloxane and acrylic polymer are then added to the drug mixture, and thoroughly mixed.

The formulation is then transferred to a coating operation where it is coated onto a protective release liner at a controlled specified thickness. The coated product is then passed through an oven in order to drive off all volatile processing solvents.

The dried product on the release liner is then joined to the backing material and wound into rolls for storage.

Appropriate size and shape "systems" are die-cut from the roll material and then pouched.

Other manufacturing methods are known in the art that are suitable for making the systems described herein.

In some embodiments, there is provided a method of effecting transdermal drug delivery of levonorgestrel (e.g., providing levonorgestrel therapy), by applying a system as described herein to the skin or mucosa of a subject in need thereof. In some embodiments, the system comprises levonorgestrel acetate, and the system is applied over a period of at least about 1 day, at least about 2 days, at least about 3 days, at least about 4 days, at least about 5 days, at least about 6 days, or at least about 7 days, such as for 1, 2, 3, 4, 5, 6 or 7 days. In some embodiments, the method is effective to achieve therapeutic levels of levonorgestrel in the subject during the application period.

The following specific examples are included as illustrative of the transdermal drug delivery systems and polymer matrices described herein. These example are in no way intended to limit the scope of the invention. Other aspects of the invention will be apparent to those skilled in the art to which the invention pertains.

EXAMPLE 1

The affect of drug loading on drug flux from a polymer matrix was determined as follows.

Polymer matrices comprising an acrylic polymer, a polysiloxane polymer, soluble PVP, and oleyl alcohol were prepared with different amounts of levonorgestrel or levonorgestrel acetate. Changes to the drug content were compensated by adjusting the amount of polysiloxane polymer.

Figure 2:
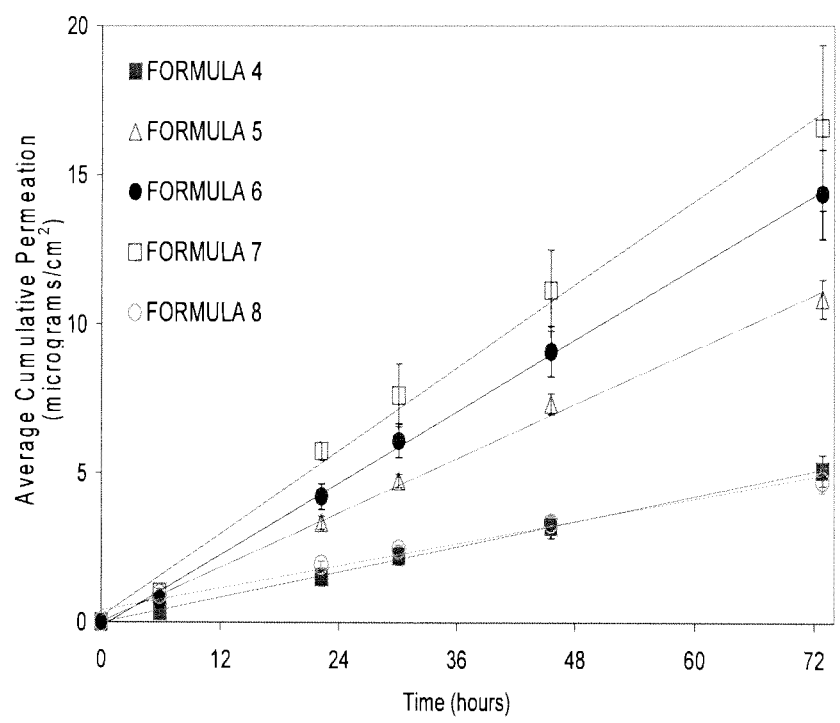
FIG. 2 illustrates the cumulative permeation flux ($\mu g/cm^2$) of levonorgestrel acetate over time (0-72 hours) from a transdermal delivery systems comprising a drug-in-adhesive polymer matrix with 0.5% (■), 1.0% (△), 1.5% (●), 3.0% (□) and 4.0% (○) by weight levonorgestrel acetate, based on the weight of the polymer matrix.

Drug flux through skin was assessed by an in vitro permeation study utilizing modified Franz cells with stratum corneum obtained from human cadaver skin. The receiver solution for this study was 0.9% NaCl with 0.01% $NaN_3$ in deionized water. Franz cells were maintained at about 32° C. for the duration of this study. Permeation samples were analyzed by high-performance liquid chromatography. The average cumulative permeation results are depicted in FIG. 1 (levonorgestrel) and FIG. 2 (levonorgestrel acetate) and the average flux rates are set forth in the tables below.

| Levonorgestrel Systems | | |
|---|---|---|
| Formulation # | Drug (%) | Flux Rate ($\mu g/cm^2/hr$) |
| 1 (■) | 0.5 | 0.1470 |
| 2 (▲) | 0.75 | 0.0253 |
| 3 (○) | 1.0 | 0.0242 |

| Levonorgestrel Acetate Systems | | |
|---|---|---|
| Formulation # | Drug (%) | Flux Rate ($\mu g/cm^2/hr$) |
| 4 (■) | 0.5 | 0.0706 |
| 5 (▲) | 1.0 | 0.1524 |
| 6 (●) | 1.5 | 0.2005 |
| 7 (□) | 3.0 | 0.2321 |
| 8 (○) | 4.0 | 0.0624 |

The data for levonorgestrel show that polymer matrices with drug concentrations greater than 0.5% by weight result in a flux that is significantly lower than polymer matrices with a lower drug load, such as about 0.5% by weight.

The data for levonorgestrel acetate show a similar effect of drug loading, but it is not observed until concentrations greater than about 3.0%.

Over all, the data show that increasing the drug load (concentration) in excess of its saturation concentration results in a significant decrease in flux for both drugs. However, while the maximum dissolved drug concentration of levonorgestrel in the tested polymer matrix was 0.5%, the maximum dissolved drug concentration of levonorgestrel acetate was 3.0%. This means that six times as much levonorgestrel acetate as levonorgestrel can be formulated in a corresponding polymer matrix without negatively impacting cumulative drug delivery or flux.

EXAMPLE 2

The maximum permeation rate achieved by the levonorgestrel and levonorgestrel acetate systems described above were compared, using levonorgestrel Formula 1 and levonorgestrel acetate Formula 7:

| Components | Levonorgestrel Formula 1 (■) | Levonorgestrel Acetate Formula 7 (Δ) |
|---|---|---|
| Levonorgestrel | 0.5 | — |
| Levonorgestrel Acetate | — | 3 |
| PVP K-30 (soluble PVP) | 10 | 10 |
| Oleyl Alcohol | 8 | 8 |
| GMS 737 (acrylic polymer) | 5 | 5 |
| BIO PSA N131-4603 (polysiloxane polymer) | 76.5 | 74 |

The flux results (obtained as described above in Example 1) are depicted in FIG. 3. The data show that the levonorgestrel acetate system achieves a permeation (flux) rate that is about 1.5 times the maximum permeation rate observed for the levonorgestrel system.

These results are surprising and unexpected. For example, while it might be expected that a product with higher drug loading would achieve transdermal delivery over a longer period of time, it is not expected that a product with higher drug loading would exhibit increased flux. Thus, the results achieved with levonorgestrel acetate go beyond that which might have been expected from its increased solubility in the polymer matrix, and may be due to improved transdermal penetration, and/or other factors.

Figure 3:
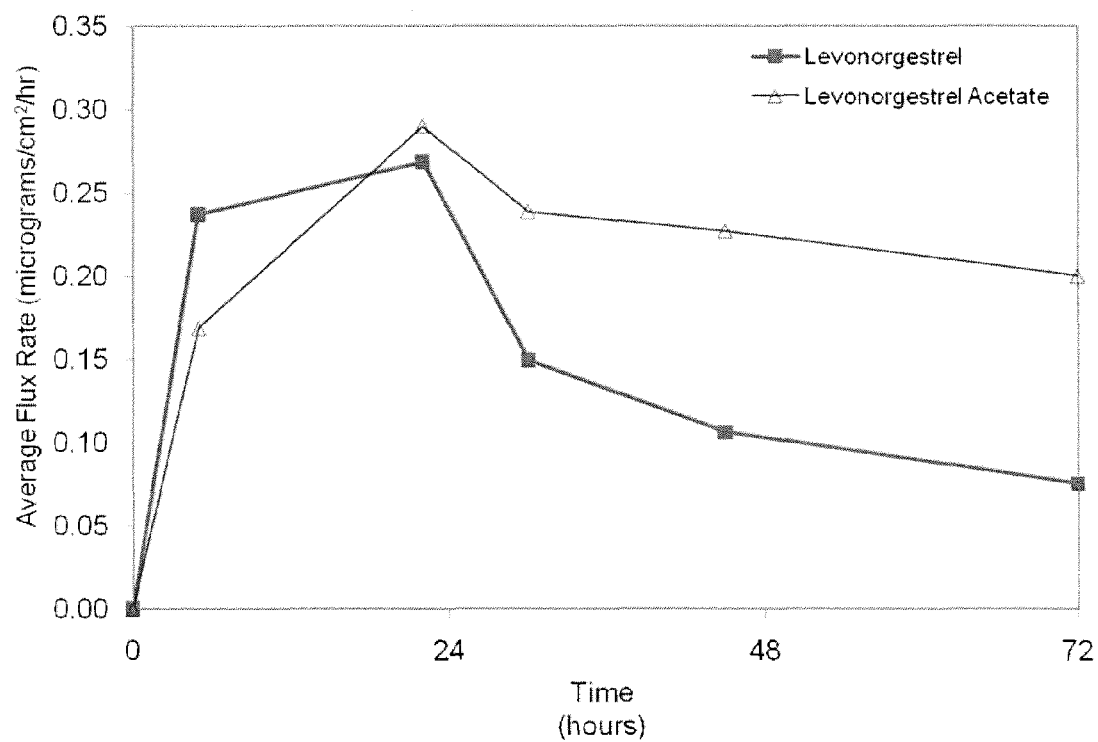
FIG. 3 illustrates the flux ($\mu g/cm^2/hr$) of levonorgestrel (■) and levonorgestrel acetate (△) over time (0-72 hours) from corresponding transdermal delivery systems, wherein the transdermal drug delivery systems each comprise amounts of levonorgestrel acetate or levonorgestrel, respectively, that are at or near but below the active agent's saturation concentration in the polymer matrix.

The results also demonstrate that the present invention permits the production of a transdermal drug delivery system for providing levonorgestrel therapy over an extended period of time, such as longer than 24 hours, including 3 days or longer, by using levonorgestrel acetate. As seen in FIG. 3, the levonorgestrel acetate product exhibits sustained flux after 24 hours through 72 hours, while the levonorgestrel product exhibits a more significant decrease in flux after 24 hours.

What is claimed is:

1. A transdermal drug delivery system comprising a polymer matrix comprising about 5-60% by weight acrylic adhesive, about 20-80% by weight silicone adhesive, about 1-20% by weight soluble PVP, up to about 15% by weight penetration enhancer, and about 1-15% by weight levonorgestrel acetate, wherein the levonorgestrel acetate is present in an amount at or below its saturation concentration in the polymer matrix.

2. The transdermal drug delivery system of claim 1, comprising from about 1% to about 15% by weight levonorgestrel acetate, based on the total weight of the polymer matrix.

3. The transdermal drug delivery system of claim 1, comprising from about 1% to about 8% by weight levonorgestrel acetate, based on the total weight of the polymer matrix.

4. The transdermal drug delivery system of claim 1, comprising from about 1% to about 6% by weight levonorgestrel acetate, based on the total weight of the polymer matrix.

5. The transdermal drug delivery system of claim 1, comprising from about 1% to about 3% by weight levonorgestrel acetate, based on the total weight of the polymer matrix.

6. The transdermal drug delivery system of claim 1, comprising from about 2% to about 6% by weight levonorgestrel acetate, based on the total weight of the polymer matrix.

7. The transdermal drug delivery system of claim 1, wherein the polymer matrix comprises about 5% by weight acrylic adhesive, about 74% by weight silicone adhesive, about 10% by weight soluble PVP, about 8.0% by weight oleyl alcohol, and about 3% by weight levonorgestrel acetate.

8. A transdermal drug delivery system comprising a polymer matrix comprising about 5-60% by weight acrylic adhesive, about 20-80% by weight silicone adhesive, about 1-20% by weight soluble PVP, up to about 15% by weight penetration enhancer, and about 1-15% by weight levonorgestrel acetate as an active agent wherein said levonorgestrel acetate transdermal drug delivery system exhibits a greater flux of the active agent than a corresponding transdermal drug delivery system comprising levonorgestrel as the active agent, wherein the transdermal drug delivery systems each comprise amounts of levonorgestrel acetate or levonorgestrel respectively, that are at or near but below the active agent's saturation concentration in the polymer matrix.

9. A transdermal drug delivery system comprising a polymer matrix, wherein the polymer matrix comprises about 5-60% by weight acrylic adhesive, about 20-80% by weight silicone adhesive, about 1-20% by weight soluble PVP, up to about 15% by weight penetration enhancer, and about 1-15% by weight levonorgestrel acetate, wherein the polymer matrix defines an active surface area, wherein said levonorgestrel acetate transdermal drug delivery system delivers at least the same amount of the active agent as a corresponding transdermal drug delivery system comprising levonorgestrel as the active agent and having an active surface area at least about 1.33 times larger than the active surface area of said levonorgestrel acetate transdermal drug delivery system.

10. A method for providing contraception or hormone replacement therapy, the method comprising administering a transdermal drug delivery system comprising a polymer matrix comprising about 5-60% by weight acrylic adhesive, about 20-80% by weight silicone adhesive, about 1-20% by weight soluble PVP, up to about 15% by weight penetration enhancer, and about 1-15% by weight levonorgestrel acetate, wherein the levonorgestrel acetate is present in an amount at or below its saturation concentration in the polymer matrix.

11. The method of claim 10, wherein the transdermal drug delivery system delivers a therapeutically effective amount of levonorgestrel acetate over an extended period of 3 days or longer.

12. A method of enhancing transdermal drug delivery of levonorgestrel, comprising providing a transdermal drug delivery system comprising a polymer matrix comprising about 5-60% by weight acrylic adhesive, about 20-80% by weight silicone adhesive, about 1-20% by weight soluble PVP, up to about 15% by weight penetration enhancer, and about 1-15% by weight levonorgestrel acetate, wherein the polymer matrix defines an active surface area, and wherein the levonorgestrel acetate is present in an amount at or below its saturation concentration in the polymer matrix.

13. The method of claim 12, wherein said levonorgestrel acetate transdermal drug delivery system exhibits a greater flux of the active agent than a corresponding transdermal drug delivery system comprising levonorgestrel as the active agent, wherein the transdermal drug delivery systems each comprise amounts of levonorgestrel acetate or levonorgestrel, respectively, that are at or near but below the active agent's saturation concentration in the polymer matrix.

14. The method of claim 12, wherein said levonorgestrel acetate transdermal drug delivery system delivers at least the same amount of active agent as a corresponding transdermal drug delivery system comprising levonorgestrel as the active agent and having an active surface area at least about 1.33 times larger than the active surface area of said levonorgestrel acetate transdermal drug delivery system.

* * * * *